United States Patent [19]
Trottmann et al.

[11] Patent Number: 6,030,984
[45] Date of Patent: Feb. 29, 2000

[54] PYRIDONE COMPOUNDS USEFUL IN TREATING ALZHEIMER'S DISEASE

[75] Inventors: Gerda Huber Trottmann, Grindel, Switzerland; Roland Jakob-Roetne, Inzlingen; Sabine Kolczewski, Lörrach, both of Germany; Roger David Norcross, Rheinfelden, Switzerland; Thomas Johannes Woltering, Weil am Rhein, Germany

[73] Assignee: Hoffmann-La Roche Inc., Nutley, N.J.

[21] Appl. No.: 09/161,853

[22] Filed: Sep. 28, 1998

Related U.S. Application Data

[62] Division of application No. 08/976,541, Nov. 24, 1997, Pat. No. 5,869,500.

[30] Foreign Application Priority Data

Dec. 13, 1996 [EP] European Pat. Off. .............. 96120050
Sep. 9, 1997 [EP] European Pat. Off. .............. 97115614

[51] Int. Cl.[7] .................... A61K 31/44; A61K 31/55; A61K 31/38; A61K 31/40; C07D 401/00
[52] U.S. Cl. .................. 514/306; 514/359; 514/211; 514/212; 514/288; 514/411; 540/597
[58] Field of Search ..................... 514/306, 359, 514/211, 212, 288, 411; 540/597

[56] References Cited

U.S. PATENT DOCUMENTS

| 4,735,940 | 4/1988 | Fischer et al. | 514/212 |
|---|---|---|---|
| 4,889,848 | 12/1989 | Fischer et al. | 514/212 |
| 5,036,066 | 7/1991 | Fischer et al. | 514/211 |
| 5,321,021 | 6/1994 | Fischer et al. | 514/211 |
| 5,707,651 | 1/1998 | Becourt et al. | 424/454 |

FOREIGN PATENT DOCUMENTS

| 0 157 346 | 3/1985 | European Pat. Off. . |
|---|---|---|
| 0 183 994 | 10/1985 | European Pat. Off. . |
| 0 398 033 | 4/1990 | European Pat. Off. . |
| 0 729 749 | 2/1996 | European Pat. Off. . |
| 0 811 378 | 12/1997 | European Pat. Off. . |
| 94/07491 | 4/1994 | Japan . |
| 96/25932 | 8/1996 | Japan . |

OTHER PUBLICATIONS

Derwent Abstract. Hata T., et al., Agent to treat conjunctivitis, chronic rheumatoid arthritis, etc.—contains quinolidinone derivative especially N–(5–(1H–tetrazolyl))–1–phenoxy–4H–quinolidine–4–one 3–carboxamide.

Imai, T., et al., Effects of a novel orally–active antiallergic drug, quinotolast (FK021), on airway clearance. 1994, Folia Pharmacol. Jpn, 104, 347–355.

Griebel, G., et al., Further Evidence for Differences Between Non–Selective and BZ–1 ( −1) Selective, Benzodiazepine Receptor Ligands in Murine Models of "State" and "Trait" Anxiety, 1996, Neuropharmacology, vol. 35, No. 8, 1081–1091.

*Primary Examiner*—Theodore J. Criares
*Attorney, Agent, or Firm*—George W. Johnston; Patricia S. Rocha-Tramaloni; Eileen M. Ebel

[57] ABSTRACT

The invention is concerned with the use of bi- and tricyclic pyridone compounds of the formula

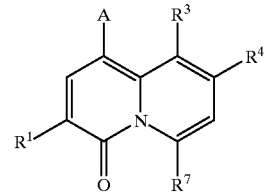

I where A, $R^1$, $R^3$, $R^4$, and $R^7$ are described herein and of their pharmaceutically acceptable salts for the production of medicaments for the prophylaxis or treatment of illnesses which are connected with an inhibition of β-amyloid peptide activity, especially for the treatment of Alzheimer's disease.

4 Claims, No Drawings

PYRIDONE COMPOUNDS USEFUL IN TREATING ALZHEIMER'S DISEASE

This is a divisional of coepending application Ser. No. 08/976,541 filed on Nov. 24, 1997 now U.S. Pat. No. 5,869,500.

The present invention is concerned with the use of bi- and tricyclic pyridone compounds as therapeutically active substances, especially for the treatment or prevention of Alzheimer's disease.

Compounds useful in the treatment or prevention of Alzheimer's disease are shown in formula I:

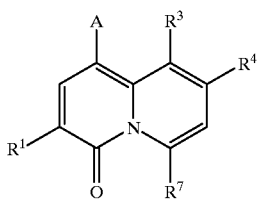

wherein
A represents hydrogen, —C(O)R$^2$ or 3-cyclopropyl-1,2,4-oxadiazol-5-yl;
R$^1$ represents phenyl optionally substituted by a group selected from trifluoromethyl, amino, hydroxy, lower-alkyl, lower-alkoxy or by a —Y—C$_6$H$_5$ group in which Y signifies a bond, —O—, —C(O)NH—, —O-lower alkyl or lower-alkyl-O—;
R$^2$ represents lower-alkyl or Q$^1$-R$^5$;
Q$^1$ represents —O— or —NR$^6$—;
R$^3$ and R$^4$ each represent hydrogen or together represent one of the groups —S—CH=CH—, —CH=CH—S—, —CH=CH—CH=CH—, —CH=CCl—CH=CH—, —N=CHN(CH$_3$)—, —S—C[CH(OH)(CH$_3$)]=CH—, —S—C(carbamoyl)=CH—, —S—C(halogen)=CH—, —S—C[C(O)OH]=CH—, —S—C(lower-alkyl)=CH— or —NH(o-phenylene);
R$^5$ represents hydrogen, lower-alkyl, lower-alkenyl, lower-alkynyl, lower-alkoxy, lower-alkoxy-alkyl, phenyl optionally substituted by lower-alkoxy, hydroxyalkyl, cycloalkyl optionally substituted by hydroxy or lower-alkoxy, benzyl optionally substituted by di-lower-alkylaminoalkyl, lower-alkanoyldialkylamino, lower-alkynyldialkylamino, lower-alkenyldialkylamino, lower-alkyldialkylamino or a saturated or aromatic 4 to 6-membered ring with at least one N, O and/or S atom, preferably with one N atom or one O atom, one N atom and one O atom, one N atom and one S atom, one S atom or two N atoms, or a saturated or aromatic bicyclic residue with optionally 1–3 hetero atoms, preferably with 3 N atoms, with the rings being bonded directly or via an alkylene, alkenylene or alkynylene group and being optionally substituted by one or more substituents selected from lower-alkyl, lower-alkoxy, hydroxy, oxo, benzyloxycarbonyl or lower-alkanoyloxyalkyl;
R$^6$ signifies hydrogen, lower-alkyl, lower-alkoxy-alkyl, cycloalkyl-lower-alkyl, phenyl, benzyl or lower-alkoxy, and wherein when
Q$^1$ is —NR$^6$—, R$^5$ and R$^6$ together can form a 4 to 6-membered saturated or aromatic heterocyclic ring with 1–2 N atoms, which is optionally substituted by one or more substituents from lower-alkoxy, lower-alkoxyalkyl, lower-hydroxyalkyl, hydroxy, halogen, lower-haloalkyl, lower-alkanoyloxyalkyl, lower-alkyl, haloalkyl or oxo; and
R$^7$ signifies hydrogen or halogen;
as well as their pharmaceutically acceptable salts.

The compounds of formula I are in part known compounds and methods for making such, being described, for example, in EP 183 994, which corresponds to U.S. Pat. Nos. 4,735,940; 4,889,848; 5,036,066; and 5,321,021, the contents of which are hereby incorporated by reference.

The possible use of these compounds as pharmaceuticals, especially for the treatment or prevention of muscular tensions, stress conditions, insomnia, anxiety states and/or convulsions, is also described in the aforementioned EP 183 994.

It has now surprisingly been found that these compounds can inhibit the formation of β-amyloid peptides, for example in cultivated cells. From the in vivo formation of β-amyloid peptides it is known that they are associated with the pathogeneses of Alzheimer's disease, whereby on the other hand this pathogenesis is also connected with the toxicity of β-amyloid peptides in human nerve cells. Accordingly, compounds which inhibit the formation of β-amyloid and thus reduce the toxicity of β-amyloid peptides in human nerve cells can be used in the prophylaxis or treatment of Alzheimer's disease.

An object of the present invention comprises the use of compounds of formula I as well as corresponding medicaments produced from them for the treatment or prevention of illnesses of the aforementioned kind, the corresponding medicaments themselves as well as novel compounds of formula IA:

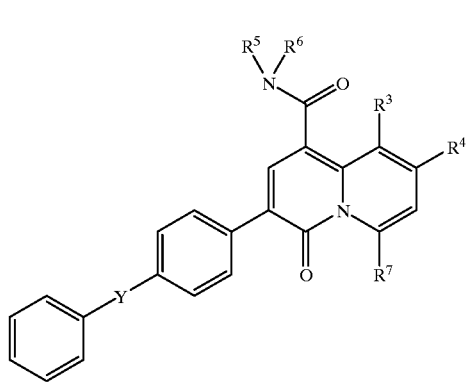

wherein R$^3$, R$^4$, R$^5$, R$^6$ and R$^7$ have the significances set forth above and Y signifies a bond, —O—, —O-lower alkyl or lower-alkyl-O—.

The term "lower" denotes residues and compounds with 1–7, preferably 1–4, carbon atoms.

The term "alkyl", taken alone or in combinations such as alkanoyl, alkanoyloxy and alkoxyalkyl, denotes straight-chain or branched-chain saturated hydrocarbon residues, preferably with 1–4 C atoms, such as methyl, ethyl, propyl, isopropyl, n-butyl, 2-butyl, isobutyl and t-butyl.

Alkenyl and alkynyl residues have 2–7, preferably 2–4, C atoms.

The term "cycloalkyl" denotes cyclic saturated hydrocarbon residues with preferably 3–7 C atoms, such as, for example, cyclohexyl.

The term "alkoxy" denotes alkyl groups bonded via an oxygen atom, such as methoxy or ethoxy.

The term "hydroxyalkyl" denotes alkyl groups substituted by hydroxy, such as 2-hydroxyethyl.

The terms "alkanoyl" and "alkanoyloxy" denote carboxylic acid residues, such as acetyl and acetoxy.

The term "alkylene" denotes straight-chain or branched-chain saturated hydrocarbon residues with two free valencies, such as methylene, 1,2-ethylene and 1,3-propylene.

The term "halogen" embraces fluorine, chlorine, bromine and iodine.

The term "saturated or aromatic 4 to 6-membered heterocyclic ring" denotes heterocycles with one or more similar or different hetero atoms, e.g. nitrogen, sulphur or oxygen, or with two hetero atoms, e.g. one oxygen atom and one nitrogen atom, one nitrogen atom and one sulphur atom or two nitrogen atoms. Examples of such heterocyclic rings are oxazole, oxadiazole, thiazole, thiazoline, thiazolidine, azetine, azetidine, pyrrole, pyrroline, pyrrolidine, morpholine, piperazine and piperidine.

Especially preferred compounds of formula I in the scope of the present invention are those in which $R^3$ and $R^4$ together form a —S—CH=CH— group. The following are examples of such compounds:

Pyridin-2-ylmethyl 7-oxo-8-phenyl-7H-thieno[2,3-a]quinolizine-10-carboxylate, 7-oxo-8-phenyl-7H-thieno[2,3-a]quinolizine-10-carboxylic acid bis-(2-methoxy-ethyl)amide, 7-oxo-8-phenyl-7H-thieno[2,3-a]quinolizine-10-carboxylic acid (2-methoxy-cyclohexyl)methyl-amide, 7-oxo-8-phenyl-7H-thieno[2,3-a]quinolizine-10-carboxylic acid (2-methoxy-ethyl)-phenyl-amide, 7-oxo-8-phenyl-7H-thieno[2,3-a]quinolizine-10-carboxylic acid thiazol-2-yl-amide, 7-oxo-8-phenyl-7H-thieno[2,3-a]quinolizine-10-carbonitrile, 10-(3-cyclopropyl-[1,2,4]oxadiazol-5-yl)-7-oxo-8-phenyl-7H-thieno[2,3-a]quinolizine, 7-oxo-8-(4-benzyloxy-phenyl)-7H-thieno[2,3-a]quinolizine-10-carboxylic acid (2-methoxy-ethyl)-phenyl-amide, 3-diethylamino-benzyl 7-oxo-8-phenyl-7H-thieno[2,3-a]quinolizine-10-carboxylate, 7-oxo-8-phenyl-7H-thieno[2,3-a]quinolizine-10-carboxylic acid 3-diethylamino-benzyl-amide, 8-(4-benzyloxy-phenyl)-7-oxo-7H-thieno[2,3-a]quinolizine-10-carboxylic acid (2-methoxy-ethyl)-pyrimidin-2-yl-amide, 8-(2-methoxy-phenyl)-7-oxo-7H-thieno[2,3-a]quinolizine-10-carboxylic acid (4-methoxy-phenyl-amide, 8-(2-methoxy-phenyl)-7-oxo-7H-thieno[2,3-a]quinolizine-10-carboxylic acid (2-methoxy-ethyl)-thiophen-2-yl-methyl-amide.

Compounds in which $R^3$ and $R^4$ together form a —CH=CCl—CH=CH— group are also preferred. One representative of this group of compounds is 10-chloro-4-oxo-3-phenyl-4H-pyrido[2,1-a]isoquinoline-1-carboxylic acid ethyl-(2-methoxy-ethyl)-amide.

Furthermore, compounds in which $R^3$ and $R^4$ together form a NH(o-phenylene) group, for example the compound methyl 4-oxo-3-phenyl-4,6,7,12-tetrahydro-indolo[2,3-a]quinolizine-1-carboxylate, are also preferred.

The compounds of formula I can be made according to methods described in EP 183 994.

Novel compounds of formula IA can be made in accordance with the invention by a) reacting a compound of the formula

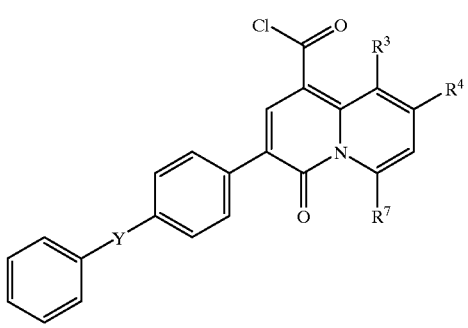

with a compound of the formula

NHR⁵R⁶    III to give a compound of formula IA, wherein the symbols have the significances given above, and b) if desired, converting the product obtained into a pharmaceutically acceptable salt.

Making the compounds of formula IA in accordance with process variant a) is effected according to generally usual methods. Preferably, the corresponding acid chloride of formula II is dissolved in dioxan, treated with an amine of formula III and stirred at room temperature for several hours.

In accordance with variant b) compounds of formula I which have one or more basic substituents can be converted into pharmaceutically acceptable salts. Such salts can be manufactured according to methods which are known per se and which will be familiar to any person skilled in the art. Salts with inorganic acids and with organic acids, for example, hydrochlorides, hydrobromides, sulphates, nitrates, citrates, acetates, maleates, succinates, methanesulphonates, p-toluenesulphonates and the like, come into consideration.

Scheme 1 hereinafter shows one method of making compounds useful in the present invention starting from known intermediates. This method is known per se and will be familiar to any person skilled in the art.

Scheme 1

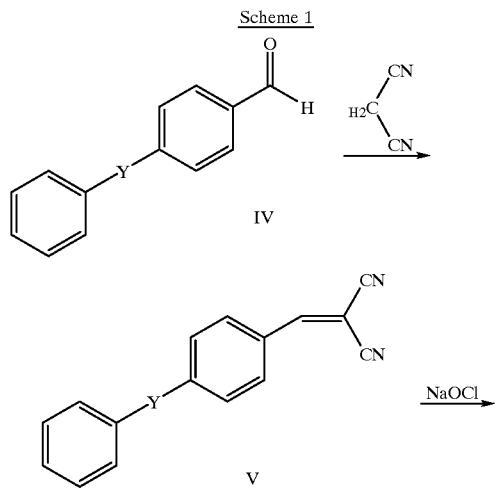

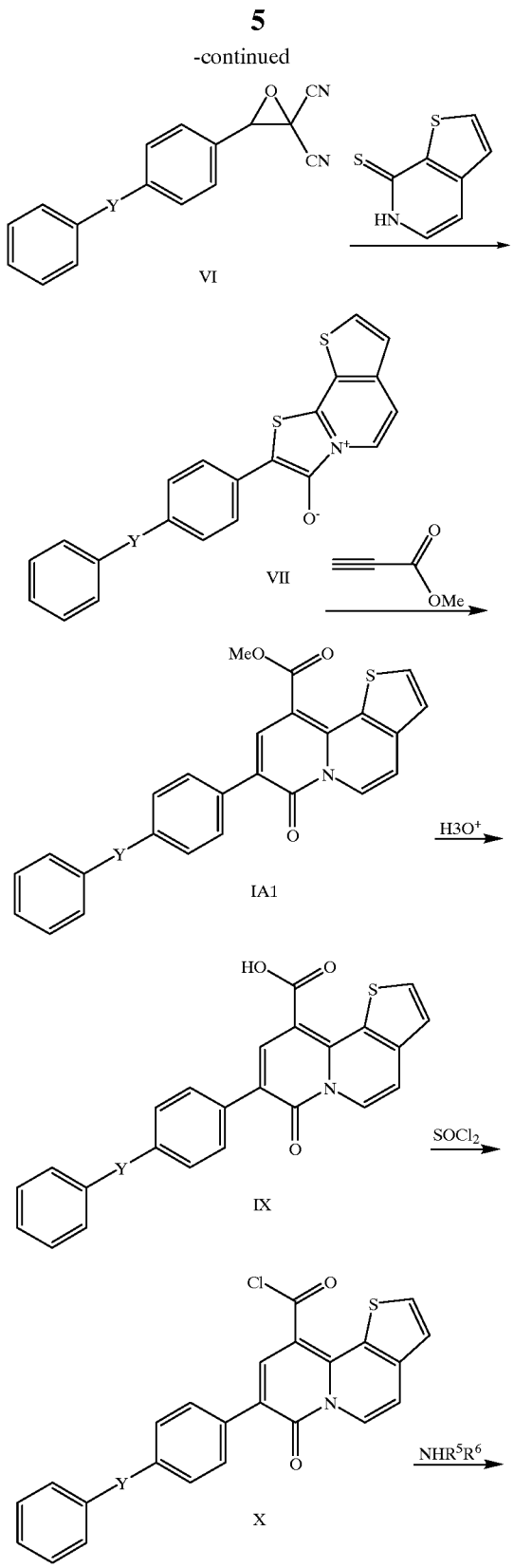

In Scheme 1 $R^5$, $R^6$ and Y have the significances given above.

The preparation of the intermediates is described in more detail in the Examples which follow.

As mentioned earlier, the compounds of formula I possess valuable pharmacological properties, since they inhibit the formation of β-amyloid-peptides and accordingly can also reduce the toxicity of β-amyloid-peptides in human nerve cells.

The term "β-amyloid peptides" denotes polypeptides from 39–43 amino acids, which have a molecular weight of about 4.2 kD. The β-amyloid-peptide with 43 amino acids has the following sequence:

Asp Ala Glu Phe Arg H is Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala Thr

Test description

The effect of test substances on the inhibition of Aβ-amyloid production can be measured in the supernatant of cell cultures of β-APP expressed cells using ELISA tests or other quantitative determination methods for β-APP degradation products. Typically, $8 \times 10^5$ cells (e.g. HEK cells, which express recombinant human β-APP variants) are plated out in each well of a culture dish having 24 wells in growth media such as e.g. OPTIMEM (Gibco) and the test compound is then added. After an incubation period of 24 to 48 hours at 37° C. in a 10% $CO_2$ atmosphere the supernatant is removed from the cell cultures and the β-APP degradation products (e.g. Aβ or β-$APP_{sec}$) are determined with the aid of ELISA (or sandwich ELISA) analysis or by means of quantitative immunoprecipitation (after metabolic radiolabelling of the cell proteins). Typically, 300 μl of the cell supernatant are tested according to the state of the art for ELISA tests in culture dishes having 96 wells. In the case of sandwich ELISA for Aβ, the binding antibody can be directed against the first 16 amino acids of Aβ-peptide (e.g. 6E10 Senetek, Maryland Heights, Mo.) and the detection antibody can be directed against amino acids 17–40 or 17–42 of Aβ and carries a detection system such as e.g. peroxidase. A simple ELISA test with an antibody, e.g. 22C11 (Boehringer Mannheim), can be used as the test for $APP_{sec}$; the second antibody can be an anti-(mouse) Ig having a detection system, such as e.g. peroxidase. The peroxidase reaction can be carried out e.g. using a TMB substrate (BioRAD) and the measurements can be carried out at 650 nm using an ELISA reading apparatus.

The following compounds 1–153 were tested, with the test results given in Table 1 being a representative selection.

1 8-Phenyl-10-(3-propoxy-azetidin-1-carbonyl)-thieno[2,3-a]quinolizin-7-one
2 2-Imidazol-1-yl-ethyl 7-oxo-8-phenyl-7H-thieno[2,3-a]quinolizine-10-carboxylate
3 5-Oxo-pyrrolidin-2-(R)-yl-methyl 7-oxo-8-phenyl-7H-thieno[2,3-a]quinolizine-10-carboxylate
4 5-Oxo-pyrrolidin-2-(S)-yl-methyl 7-oxo-8-phenyl-7H-thieno[2,3-a]quinolizine-10-carboxylate
5 2-(2-Oxo-oxazolidin-3-yl)-ethyl 7-oxo-8-phenyl-7H-thieno[2,3-a]quinolizine-10-carboxylate
6 Pyridin-2-yl-methyl 7-oxo-8-phenyl-7H-thieno[2,3-a]quinolizine-10-carboxylate
7 10-(3-Oxo-azetidin-1-carbonyl)-8-phenyl-thieno[2,3-a]quinolizin-7-one
8 10-(4-Methoxy-2-methoxymethyl-pyrrolidine-1-carbonyl)-8-phenyl-thieno[2,3-a]quinolizin-7-one
9 10-(3-Ethoxy-pyrrolidine-1-carbonyl)-8-phenyl-thieno[2,3-a]quinolizin-7-one
10 8-Phenyl-10-(3-propoxy-pyrrolidine-1-carbonyl)-thieno[2,3-a]quinolizin-7-one
11 10-(2-(R)-Iodomethyl-pyrrolidine-1-carbonyl)-8-phenyl-thieno[2,3-a]quinolizin-7-one
12 1-(7-Oxo-8-phenyl-7H-thieno[2,3-a]quinolizine-10-carbonyl)-pyrrolidin-2-(R)-yl-methyl acetate
13 10-(4-Methoxy-piperidine-1-carbonyl)-8-phenyl-thieno[2,3-a]quinolizin-7-one
14 10-(3-Methoxy-piperidine-1-carbonyl)-8-phenyl-thieno[2,3-a]quinolizine-7-on
15 Methyl 7-oxo-8-phenyl-7H-thieno[2,3-a]quinolizine-10-carboxylate
16 Ethyl [4-(7-oxo-8-phenyl-7H-thieno[2,3-a]quinolizine-10-carbonyl)-piperazin-1-yl]-acetate methanesulphonate
17 Methyl 4-oxo-3-(trifluoromethyl-phenyl)-4H-quinolizine-1-carboxylate
18 7-Oxo-8-phenyl-7H-thieno[2,3-a]quinolizine-10-carboxylic acid (3-methoxy-propyl)-methyl-amide
19 7-Oxo-8-phenyl-7H-thieno[2,3-a]quinolizine-10-carboxylic acid (2-methoxy-ethyl)-methyl-amide
20 7-Oxo-8-phenyl-7H-thieno[2,3-a]quinolizine-10-carboxylic acid (2-methoxy-ethyl)-ethyl-amide
21 7-Oxo-8-phenyl-7H-thieno[2,3-a]quinolizine-10-carboxylic acid (2-hydroxy-ethyl)-ethyl-amide
22 7-Oxo-8-phenyl-7H-thieno[2,3-a]quinolizine-10-carboxylic acid bis-(2-methoxy-ethyl)-amide
23 7-Oxo-8-phenyl-7H-thieno[2,3-a]quinolizine-10-carboxylic acid (2-methoxy-ethyl)phenyl-amide
24 7-Oxo-8-phenyl-7H-thieno[2,3-a]quinolizine-10-carboxylic acid methyl-(tetrahydrofuran-2-yl-methyl)-amide
25 7-Oxo-8-phenyl-7H-thieno[2,3-a]quinolizine-10-carboxylic acid (2-hydroxy-cyclohexyl-amide
26 7-Oxo-8-phenyl-7H-thieno[2,3-a]quinolizine-10-(2-methoxy-cyclohexyl)-methyl-amide
27 1-Methyl-1H-imidazol-2-yl-methyl 7-oxo-8-phenyl-7H-thieno[2,3-a]quinolizine-10-carboxylate methanesulphonate
28 1-Methyl-pyrrolidin-2-(S)-yl-methyl 7-oxo-8-phenyl-7H-thieno[2,3-a]quinolizine-10-carboxylate
29 2-(2-Oxo-pyrrolidin-1-yl)-ethyl 7-oxo-8-phenyl-7H-thieno[2,3-a]quinolizine-10-carboxylate
30 Dimethyl-carbamoylmethyl 7-oxo-8-phenyl-7H-thieno[2,3-a]quinolizine-10-carboxylate
31 2-(S)-Amino-4-methyl-pentyl 7-oxo-8-phenyl-7H-thieno[2,3-a]quinolizine-10-carboxylate
32 2-Morpholin-4-yl-ethyl 7-oxo-8-phenyl-7H-thieno[2,3-a]quinolizine-10-carboxylate hydrochloride
33 Methyl 4-oxo-3-phenyl-4H-quinolizine-1-carboxylate
34 10-(2-(S)-Methoxymethyl-pyrrolidine-1-carbonyl)-8-phenyl-thieno[2,3-a]quinolizin-7-one
35 10-(2-(R)-Methoxymethyl-pyrrolidine-1-carbonyl)-8-phenyl-thieno[2,3-a]quinolizin-7-one
36 Methyl 10-chloro-4-oxo-3-phenyl-4H-pyrido[2,1-a]isoquinoline-1-carboxylate
37 10-Chloro-1-(2-methoxymethyl-pyrrolidine-1-carbonyl)-3-phenyl-pyrido[2,1-a]isoquinolin-4-one
38 10-Chloro-1-(2-(R)methoxymethyl-pyrrolidine-1-carbonyl)-3-phenyl-pyrido[2,1-a]isoquinolin-4-one
39 10-(3-Methoxy-azetidine-1-carbonyl)-8-phenyl-thieno[2,3-a]quinolizin-7-one
40 10-Chloro-1-(3-methoxy-azetidine-1-carbonyl)-3-phenyl-pyrido[2,1-a]isoquinolin-4-one 41 10-Chloro-1-(3-methoxy-pyrrolidine-1-carbonyl)-3-phenyl-pyrido[2,1-a]isoquinolin-4-one
42 10-Chloro-4-oxo-3-phenyl-4H-pyrido[2,1-a]isoquinoline-1-carboxylic acid ethyl-(2-methoxy-ethyl)-amide
43 2,5-Dioxo-pyrrolidin-1-yl 7-oxo-8-phenyl-7H-thieno[2,3-a]quinolizine-10-carboxylate
44 10-(2-(R)-Hydroxymethyl-pyrrolidine-1-carbonyl)-8-(4-hydroxy-phenyl)-thieno[2,3-a]quinolizin-7-one
45 10-(3,5-Dimethyl-pyrazole-1-carbonyl)-8-phenyl-thieno[2,3-a]quinolizin-7-one
46 4-(Morpholin-4-yl)-but-2-ynyl 7-oxo-8-phenyl-7H-thieno[2,3-a]quinolizine-10-carboxylate
47 4-(Pyrrolidin-1-yl)-but-2-ynyl 7-oxo-8-phenyl-7H-thieno[2,3-a]quinolizine-10-carboxylate methanesulphonate
48 4-Diisopropylamino-but-2-ynyl 7-oxo-8-phenyl-7H-thieno[2,3-a]quinolizine-10-carboxylate methanesulphonate
49 7-Oxo-8-phenyl-7H-thieno[2,3-a]quinolizine-10-carboxylic acid thiazol-2-yl-amide
50 10-(2-Methoxymethyl-piperidine-1-carbonyl)-8-phenyl-thieno[2,3-a]quinolizin-7-one
51 10-(3-Isopropoxy-pyrrolidine-1-carbonyl)-8-phenyl-thieno[2,3-a]quinolizin-7-one
52 10-(Imidazole-1-carbonyl)-8-phenyl-thieno[2,3-a]quinolizin-7-one
53 2-Dimethylamino-ethyl 7-oxo-8-phenyl-7H-thieno[2,3-a]quinolizine-10-carboxylate hydrochloride
54 7-Oxo-8-phenyl-7H-thieno [2,3-a]quinolizine-10-carboxylic acid methoxy-methyl-amide
55 Thiophen-2-yl-methyl 7-oxo-8-phenyl-7H-thieno[2,3-a]quinolizine-10-carboxylate
56 7-Oxo-8-phenyl-7H-thieno[2,3-a]quinolizine-10-carboxylic acid amide
57 (3RS,4SR)-1-Benzyloxy-carbonyl-4-hydroxy-pyrrolidin-3-yl 7-oxo-8-phenyl-7H-thieno[2,3-a]quinolizine-10-carboxylate
58 10-Acetyl-8-phenyl-thieno[2,3-a]quinolizine-7-one
59 4-Dimethylamino-but-2-enyl 7-oxo-8-phenyl-7H-thieno[2,3-a]quinolizine-10-carboxylate methanesulphonate 60 3-Diethylamino-methyl-benzyl 7-oxo-8-phenyl-7H-thieno[2,3-a]quinolizine-10-carboxylate methanesulphonate
61 7-Oxo-8-phenyl-7H-thieno[2,3-a]quinolizine-10-carboxylic acid 3-diethylamino-methyl-benzyl-amide methanesulphonate
62 10-(3-Cyclopropyl-[1,2,4]oxadiazol-5-yl)-8-phenyl-thieno[2,3-a]quinolizin-7-one
63 Methyl 4-oxo-3-phenyl-4,6,7,12-tetrahydro-indolo[2,3-a]quinolizine-1-carboxylate
64 8-(3-Methoxy-phenyl)-thieno[2,3-a]quinolizin-7-one
66 8-(4-Benzyloxy-phenyl)-7-oxo-7H-thieno[2,3-a]quinolizine-10-carboxylic acid (2-methoxy-ethyl)-amide
67 8-(4-Benzyloxy-phenyl)-7-oxo-7H-thieno[2,3-a]quinolizine-10-carboxylic acid bis-(2-methoxy-ethyl)-amide
68 8-(4-Benzyloxy-phenyl)-7-oxo-7H-thieno[2,3-a]quinolizine-10-carboxylic acid ethyl-(2-methoxy-ethyl)-amide
69 8-(4-Benzyloxy-phenyl)-7-oxo-7H-thieno[2,3-a]quinolizine-10-carboxylic acid isopropyl-(2-methoxy-ethyl)-amide
70 8-(4-Benzyloxy-phenyl)-7-oxo-7H-thieno[2,3-a]quinolizine-10-carboxylic acid cyclopropylmethyl-(2-methoxy-ethyl)-amide
71 8-(4-Benzyloxy-phenyl)-7-oxo-7H-thieno[2,3-a]quinolizine-10-carboxylic acid benzyl-(2-methoxy-ethyl)-amide
72 8-(4-Benzyloxy-phenyl)-7-oxo-7H-thieno[2,3-a]quinolizine-10-carboxylic acid (2-methoxy-ethyl)-phenyl-amide
73 8-(4-Benzyloxy-phenyl)-7-oxo-7H-thieno[2,3-a]quinolizine-10-carboxylic acid (2-hydroxy-ethyl)-phenyl-amide
74 8-(4-Benzyloxy-phenyl)-2-methyl-7-oxo-7H-thieno[2,3-a]quinolizine-10-carboxylic acid (2-methoxy-ethyl)-phenyl)-amide
75 (RS)-8-(4-Benzyloxy-phenyl)-2-(1-hydroxy-ethyl)-7-oxo-7H-thieno[2,3-a]quinolizine-10-carboxylic acid (2-methoxy-ethyl)-phenyl-amide
76 8-(4-Benzyloxy-phenyl)-7-oxo-7H-thieno[2,3-a]quinolizine-2,10-dicarboxylic acid 2-dimethylamide 10-[(2-methoxy-ethyl)-phenyl-amide]
77 8-(4-Benzyloxy-phenyl)-2-bromo-7-oxo-7H-thieno[2,3-a]quinolizine-10-carboxylic acid (2-methoxy-ethyl)-phenyl-amide
78 8-(4-Benzyloxy-phenyl)-2-ethyl-7-oxo-7H-thieno[2,3-a]quinolizine-10-carboxylic acid (2-methoxy-ethyl)-phenyl-amide
79 8-(4-Benzyloxy-phenyl)-2-propyl-7-oxo-7H-thieno[2,3-a]quinolizine-10-carboxylic acid (2-methoxy-ethyl)-phenyl-amide
80 8-(4-Benzyloxy-phenyl)-10-[(2-methoxy-ethyl)-phenyl-carbamoyl]-7-oxo-7H-thieno[2,3-a]quinolizine-2-carboxylic acid
81 8-(4-Benzyloxy-phenyl)-2-iodo-7-oxo-7H-thieno[2,3-a]quinolizine-10-carboxylic acid (2-methoxy-ethyl)-phenyl-amide
82 8-(4-Benzyloxy-phenyl)-7-oxo-7H-thieno[2,3-a]quinolizine-10-carboxylic acid 4-diethylaminoethyl-benzyl-amide
83 8-(4-Benzyloxy-phenyl)-2-bromo-7-oxo-7H-thieno[2,3-a]quinolizine-10-carboxylic acid (2-methoxy-ethyl)-phenyl-amide
84 8-(4-Benzyloxy-phenyl)-5-bromo-7-oxo-7H-thieno[2,3-a]quinolizine-10-carboxylic acid (2-methoxy-ethyl)-phenyl-amide
85 8-(4-Benzyloxy-phenyl)-2,5-dibromo-7-oxo-7H-thieno[2,3-a]quinolizine-10-carboxylic acid (2-methoxy-ethyl)-phenyl-amide
86 8-(4-Benzyloxy-phenyl)-7-oxo-2-trifluoromethyl-7H-thieno[2,3-a]quinolizine-10-carboxylic acid (2-methoxy-ethyl)-phenyl-amide
87 8-(4-Benzyloxy-phenyl)-7-oxo-7H-thieno[2,3-a]quinolizine-10-carboxylic acid (2-methoxy-ethyl)-(pyridin-3-ylmethyl)-amide
88 8-(4-Benzyloxy-phenyl)-7-oxo-7H-thieno[2,3-a]quinolizine-10-carboxylic acid (2-morpholin-4yl-ethyl)-phenyl-amide
89 8-(4-Benzyloxy-phenyl)-7-oxo-7H-thieno[2,3-a]quinolizine-10-carboxylic acid 4-diethylamino-benzyl-amide
90 8-(4-Benzyloxy-phenyl)-7-oxo-7H-thieno[2,3-a]quinolizine-10-carboxylic acid (2-methoxy-ethyl)-pyrimidin-2-yl-amide
91 8-(4-Benzyloxy-phenyl)-7-oxo-7H-thieno[2,3-a]quinolizine-10-carboxylic acid (2-methoxy-ethyl)-(3-methyl-isothiazol-5-yl)-amide
92 Methyl 8-(biphenyl-4-yl)-7-oxo-7H-thieno[2,3-a]quinolizine-10-carboxylate
93 8-(Biphenyl-4-yl)-7-oxo-7H-thieno[2,3-a]quinolizine-10-carboxylic acid ethyl-(2-methoxy-ethyl)-amide
94 Ethyl 8-(biphenyl-4-yl)-7-oxo-7H-thieno[2,3-a]quinolizine-10-carboxylate
95 8-(Biphenyl-4-yl)-7-oxo-7H-thieno[2,3-a]quinolizine-10-carboxylic acid bis-(2-methoxy-ethyl)-amide
96 Methyl 7-oxo-8-(4-phenoxy-phenyl)-7H-thieno[2,3-a]quinolizine-10-carboxylate
97 7-Oxo-8-(4-phenoxy-phenyl)-7H-thieno[2,3-a]quinolizine-10-carboxylic acid bis-(2-methoxy-ethyl)-amide
98 7-Oxo-8-(4-phenoxy-phenyl)-7H-thieno[2,3-a]quinolizine-10-carboxylic acid (2-methoxy-ethyl)-amide
99 7-Oxo-8-(4-phenoxy-phenyl)-7H-thieno[2,3-a]quinolizine-10-carboxylic acid ethyl-(2-methoxy-ethyl)-amide
100 7-Oxo-8-(4-phenoxy-phenyl)-7H-thieno[2,3-a]quinolizine-10-carboxylic acid benzyl-(2-methoxy-ethyl)-amide
101 7-Oxo-8-(4-phenoxy-phenyl)-7H-thieno[2,3-a]quinolizine-10-carboxylic acid (2-methoxy-ethyl)-phenyl-amide
102 8-(4-Benzyloxy-phenyl)-3-methyl-7-oxo-3,7-dihydro-imidazo[4,5-a]quinolizine-10-carboxylic acid (2-methoxy-ethyl)-phenyl-amide
103 8-(4-Benzyloxy-phenyl)-3-methyl-7-oxo-3,7-dihydro-imidazo [4,5-a]quinolizine-10-carboxylic acid bis-(2-methoxy-ethyl)-amide
104 8-(4-Benzyloxy-phenyl)-3-methyl-7-oxo-3,7-dihydro-imidazo[4,5-a]quinolizine-10-carboxylic acid cyclopropylmethyl-(2-methoxy-ethyl)-amide
105 8-(4-Benzyloxy-phenyl)-3-methyl-7-oxo-3,7-dihydro-imidazo [4,5-a]quinolizine-10-carboxylic acid (2-methoxy-ethyl)-propyl-amide
106 Methyl 8-(4-tert-butyl-phenyl)-7-oxo-7H-thieno[2,3-a]quinolizine-10-carboxylate 107 8-(4-tert-Butyl-phenyl)-7-oxo-7H-thieno[2,3-a]quinolizine-10-carboxylic acid ethyl-(2-methoxy-ethyl)-amide 108 8-(4-tert-Butyl-phenyl)-7-oxo-7H-thieno[2,3-a]quinolizine-10-carboxylic acid (2-methoxy-ethyl)-propyl-amide 109 8-(4-tert-Butyl-phenyl)-7-oxo-7H-thieno[2,3-a]quinolizine-10-carboxylic acid bis-(2-methoxy-ethyl)-amide 110 8-(4-tert-Butyl-phenyl)-7-oxo-7H-thieno[2,3-a]quinolizine-10-carboxylic acid (2-methoxy-ethyl)-amide 111 8-(4-tert-Butyl-phenyl)-7-oxo-7H-thieno[2,3-a]quinolizine-10-carboxylic acid (2-methoxy-ethyl)-phenyl-amide 112 8-(4-tert-Butyl-phenyl)-7-oxo-7H-thieno[2,3-a]quinolizine-10-carboxylic acid cyclopropylmethyl-(2-methoxy-ethyl)-amide 113 8-(4-tert-Butyl-phenyl)-7-oxo-7H-thieno[2,3-a]quinolizine-10-carboxylic acid benzyl-(2-methoxy-ethyl)-amide 114 Methyl 8-(2-methoxy-phenyl)-7-oxo-7H-thieno[2,3-a]quinolizine-10-carboxylate 115 8-(2-Methoxy-phenyl)-7-oxo-7H-thieno[2,3-a]quinolizine-10-carboxylic acid (2-methoxy-ethyl)-amide 116 8-(3-Methoxy-phenyl)-7-oxo-7H-thieno[2,3-a]quinolizine-10-carboxylic acid benzyl-amide 117 8-(3-Methoxy-phenyl)-7-oxo-7H-thieno[2,3-a]quinolizine-10-carboxylic acid cyclopentyl-(2-methoxy-ethyl)-amide 118 8-(3-Methoxy-phenyl)-7-oxo-7H-thieno[2,3-a]quinolizine-10-carboxylic acid cyclopropylmethyl-amide 119 8-(2-Methoxy-phenyl)-7-oxo-7H-thieno[2,3-a]quinolizine-10-carboxylic acid cyclopropylmethyl-(2-methoxy-ethyl)-amide 120 8-(2-Methoxy-phenyl)-7-oxo-7H-thieno[2,3-a]quinolizine-10-carboxylic acid benzyl-(2-methoxy-ethyl)-amide 121 8-(2-Methoxy-phenyl)-7-oxo-7H-thieno[2,3-a]quinolizine-10-carboxylic acid (2-methoxy-ethyl)-phenyl-amide 122 8-(2-Methoxy-phenyl)-7-oxo-7H-thieno[2,3-a]quinolizine-10-carboxylic acidethyl-(2-methoxy-ethyl)-amide 123 8-(3-Methoxy-phenyl)-7-oxo-7H-thieno[2,3-a]quinolizine-10-carboxylic acid (3,4-dimethoxy-phenyl)-amide 124 8-(3-Methoxy-phenyl)-7-oxo-7H-thieno[2,3-a]quinolizine-10-carboxylic acid pyridin-4yl-amide 125 8-(3-Methoxy-phenyl)-7-oxo-7H-thieno[2,3-a]quinolizine-10-carboxylic acid (2-methoxy-ethyl)-thiophen-2-yl-methyl-amide 126 8-(3-Methoxy-phenyl)-7-oxo-7H-thieno[2,3-a]quinolizine-10-carboxylic acid (furan-2-yl-methyl)-(2-methoxy-ethyl)-amide 127 8-(3-Methoxy-phenyl)-7-oxo-7H-thieno[2,3-a]quinolizine-10-carboxylic acid phenyl-prop-2-ynyl-amide 128 8-(3-Methoxy)-phenyl)-7-oxo-7H-thieno[2,3-a]quinolizine-10-carboxylic acid (3,4-dimethoxy-phenyl)-amide 129 Methyl 8-(2-methoxy-phenyl)-7-oxo-7H-thieno[2,3-a]quinolizine-10-carboxylate 130 8-(2-Methoxy-phenyl)-7-oxo-7H-thieno[2,3-a]quinolizine-10-carboxylic acid (2-morpholin-4-yl-ethyl)-phenyl-amide 131 8-(2-Methoxy-phenyl)-7-oxo-7H-thieno[2,3-a]quinolizine-10-carboxylic acid diethylamino-benzyl-amide 132 8-(2-Methoxy-phenyl)-7-oxo-7H-thieno[2,3-a]quinolizine-10-carboxylic acid cyclopropylmethyl-amide 133 Benzotriazol-1-yl 8-(2-methoxy-phenyl)-7-oxo-7H-thieno[2,3-a]quinolizine-10-carboxylate 134 8-(2-Methoxy-phenyl)-7-oxo-7H-thieno[2,3-a]quinolizine-10-carboxylic acid cyclopentyl-(2-methoxy-ethyl)-amide 135 8-(2-Methoxy-phenyl)-7-oxo-7H-thieno[2,3-a]quinolizine-10-carboxylic acid benzyl-amide 136 8-(2-Methoxy-phenyl)-7-oxo-7H-thieno[2,3-a]quinolizine-10-carboxylic acid (4-diethylaminomethyl)-benzyl-amide 137 8-(2-Methoxy-phenyl)-7-oxo-7H-thieno[2,3-a]quinolizine-10-carboxylic acid (3-diethylamino-methyl)-benzyl-amide 138 3-Diethylamino-methyl-benzyl 8-(2-methoxy-phenyl)-7-oxo-7H-thieno[2,3-a]quinolizine-10-carboxylate 139 8-(2-Methoxy-phenyl)-7-oxo-7H-thieno[2,3-a]quinolizine-10-carboxylic acid (furan-2-yl-methyl)-(2-methoxy-ethyl)-amide 140 8-(2-Methoxy-phenyl)-7-oxo-7H-thieno[2,3-a]quinolizine-10-carboxylic acid (2-methoxy-ethyl)-thiophen-2-yl-methyl-amide 141 8-(2-Methoxy-phenyl)-7-oxo-7H-thieno[2,3-a]quinolizine-10-carboxylic acid (3,4-dimethoxy-phenyl)-amide 142 8-(2-Methoxy-phenyl)-7-oxo-7H-thieno[2,3-a]quinolizine-10-carboxylic acid (4-methoxy-phenyl)-amide 143 8-(2-Methoxy-phenyl)-7-oxo-7H-thieno[2,3-a]quinolizine-10-carboxylic acid phenyl-prop-2-ynyl-amide 144 8-(4-Methoxy-phenyl)-7-oxo-7H-thieno[2,3-a]quinolizine-10-carboxylic acid ethyl-(2-methoxy-ethyl)-amide 145 8-(4-Methoxy-phenyl)-7-oxo-7H-thieno[2,3-a]quinolizine-10-carboxylic acid bis-(2-methoxy-ethyl)-amide 146 8-(4-Methoxy-phenyl)-7-oxo-7H-thieno[2,3-a]quinolizine-10-carboxylic acid cyclopropylmethyl-(2-methoxy-ethyl)-amide 147 8-(4-Methoxy-phenyl)-7-oxo-7H-thieno[2,3-a]quinolizine-10-carboxylic acid (2-methoxy-ethyl)-phenyl-amide 148 8-(4-Methoxy-phenyl)-7-oxo-7H-thieno[2,3-a]quinolizine-10-carboxylic acid (2-methoxy-ethyl)-propyl-amide 149 7-Oxo-8-p-tolyl-7H-thieno[2,3-a]quinolizine-10-carboxylic acid ethyl-(2-methoxy-ethyl)-amide 150 7-Oxo-8-p-tolyl-7H-thieno[2,3-a]quinolizine-10-carboxylic acid bis-(2-methoxy-ethyl)-amide 151 Ethyl 7-oxo-8-p-tolyl-7H-thieno[2,3-a]quinolizine-10-carboxylate 152 8-(2-Benzoylamino-phenyl)-7-oxo-8-p-tolyl-7H-thieno[2,3-a]quinolizine-10-carboxylic acid (2-methoxy-ethyl)-phenyl-amide 153 8-(2-Amino-phenyl)-7-oxo-7H-thieno[2,3-a]chinolizine-10-carboxylic acid (2-methoxy-ethyl)-phenyl-amide The following Table 1 shows the inhibition of Aβ production in cellular tests. SE-SFAD signifies the Aβ production inhibition measured using sandwich-ELISA in HEK cells, SFAD signifies over-expressed mutated β-APP, and SE-WT signifies the Aβ production inhibition measured using sandwich-ELISA in HEK cells which over-express Wild type β-APP. The $IC_{50}$ values are based on the respective plateau of inhibition.

TABLE 1

| Compound | SE-SFAD $IC_{50}$ [μM] | SE-SFAD max. inhibition (%) | SE-WT $IC_{50}$ [μM] | SE-WT max. inhibition (%) |
|---|---|---|---|---|
| 1 | 2 | 65 | 4 | 75 |
| 2 | 10 | 50 | 1.2 | 70 |
| 3 | 9.5 | 30 | 1 | 60 |
| 4 | 10 | 25 | 5 | 25 |
| 5 | 1 | 25 | 1.2 | 60 |
| 6 | 3 | 50 | 0.6 | 75 |
| 7 | 50 | 100 | | |
| 8 | 1 | 35 | 12 | 25 |
| 9 | 5 | 35 | 40 | 50 |
| 10 | 6.6 | 50 | 7 | 50 |
| 11 | | | 11 | 100 |
| 12 | | | 1 | 50 |
| 13 | 5 | 30 | 4 | 80 |
| 14 | 2.3 | 50 | 8 | 70 |
| 15 | 3.0 | 60 | | |
| 16 | 3 | 30 | 6 | 70 |
| 17 | 0.5 | 30 | | |
| 18 | 4 | 30 | 7 | 40 |
| 19 | | | 20 | 100 |
| 20 | 15 | 30 | 9 | 70 |
| 21 | | | 40 | 100 |
| 22 | 2 | 80 | 2.5 | 80 |
| 23 | 6.7 | 100 | 3.4 | 100 |
| 24 | 7 | 40 | 10 | 60 |
| 25 | 10 | 100 | | |
| 26 | 5 | 80 | 1.2 | 100 |
| 27 | 50 | 100 | | |
| 28 | 9 | 100 | 2 | 100 |
| 29 | 3 | 40 | 4.1 | 80 |
| 30 | 5 | 25 | 5 | 60 |
| 31 | 5.3 | 100 | 1.2 | 55 |
| 32 | 30 | 100 | 3 | 100 |
| 33 | 6 | 40 | 5 | 40 |
| 34 | 9 | 50 | 4 | 60 |
| 35 | 6 | 50 | 3 | 65 |
| 36 | 2.8 | 40 | 1 | 60 |
| 37 | 7 | 100 | 1 | 70 |
| 38 | 7 | 100 | 1.5 | 70 |
| 39 | 7 | 30 | 6 | 50 |
| 40 | 6.8 | 100 | 7 | 70 |
| 41 | 6 | 100 | 3.5 | 75 |
| 42 | 3 | 100 | 0.9 | 100 |
| 43 | 2 | 50 | 5 | 70 |
| 44 | 6 | 50 | 5 | 50 |
| 45 | 0.9 | 40 | 0.5 | 30 |
| 46 | 4 | 70 | 1 | 50 |
| 47 | 5 | 55 | 1.5 | 55 |
| 48 | 12 | 100 | 3.3 | 100 |
| 49 | 0.7 | 50 | 0.5 | 50 |
| 50 | 5.5 | 40 | 3.6 | 40 |
| 51 | 60 | 100 | 24 | 100 |
| 52 | 5 | 25 | 12 | 45 |
| 53 | 9.5 | 80 | 8 | 100 |
| 54 | 6 | 30 | 3 | 40 |
| 55 | 4 | 50 | 5 | 60 |
| 56 | 1 | 35 | | |
| 57 | 0.5 | 35 | | |
| 58 | 1 | 60 | 0.2 | 40 |
| 59 | 5 | 100 | 7 | 100 |
| 60 | 1.2 | 100 | | |
| 62 | 0.5 | 65 | 2.7 | 80 |
| 63 | 1 | 65 | 0.6 | 45 |
| 66 | 22 | 60 | | |
| 67 | 0.8 | 70 | 0.6 | 80 |
| 68 | 8 | 25 | | |
| 69 | 0.8 | 45 | | |
| 70 | <1 | 100 | | |
| 71 | 0.57 | 100 | | |
| 72 | 0.5 | 100 | | |
| 73 | 1.3 | 55 | | |
| 74 | 0.3 | 100 | | |
| 75 | 1.3 | 100 | | |
| 76 | 2.8 | 40 | | |
| 77 | 0.2 | 80 | 0.2 | 100 |
| 78 | | 40 | | |
| 79 | | 20–35 | | |
| 80 | 1–3 | 30–70 | | |
| 81 | <1 | 50 | 1.2 | 100 |
| 83 | 0.2 | 80 | 0.2 | 100 |
| 93 | 4.2 | 100 | | |
| 94 | | 20–40 | | |
| 95 | 1.3 | 100 | | |
| 96 | 1 | 40 | | |
| 97 | 2.2 | 100 | | |
| 98 | 2.4 | 70–90 | | |
| 99 | 2.5 | 100 | | |
| 100 | 0.6 | 100 | | |
| 101 | 0.9 | 100 | | |
| 102 | 3.6 | 80 | | |
| 103 | 5 | 35–55 | | |
| 104 | 3 | 100 | | |
| 105 | 5 | 50 | | |
| 106 | 2.3 | 85 | 0.8 | 95 |
| 107 | 3 | 20 | | |
| 108 | 1.4 | 100 | 1 | 100 |
| 109 | 7.7 | 100 | 0.8 | 100 |
| 110 | 6.2 | 95 | | |
| 111 | 2.5 | 100 | | |
| 112 | 1.5 | 100 | | |
| 113 | 3 | 100 | | |
| 114 | 6.3 | 70 | | |
| 115 | 20 | 50 | | |
| 116 | 0.8 | 100 | 1 | 60–80 |
| 119 | 1.6 | 60–80 | | |
| 120 | 1.8 | 100 | | |
| 121 | 1.8 | 100 | | |
| 122 | 8 | 25 | | |
| 123 | 0.8 | 100 | | |
| 124 | 0.8 | 35 | | |
| 125 | 2 | 10 | | |
| 127 | 0.8 | 100 | | |
| 129 | 2.8 | 75 | 1.5 | 85 |
| 135 | 3 | 100 | | |
| 139 | 3.3 | 100 | | |
| 140 | 2.5 | 30–100 | | |
| 142 | 1.5 | 20–100 | | |
| 143 | 5.5 | 40–100 | | |
| 144 | 2 | 40 | | |
| 145 | 5 | 100 | | |
| 146 | 1.5 | 100 | | |
| 147 | 1.5 | 100 | | |
| 148 | 5 | 100 | | |
| 149 | 2.4 | 100 | | |
| 150 | 2.7 | 100 | | |
| 151 | 0.8 | 100 | | |
| 152 | 1.4 | 100 | 1.5 | 50–90 |
| 153 | | 20–40 | | |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. However, the administration can also be effected rectally, e.g. in the form of suppositories, parenterally, e.g. in the form of injection solutions, or transdermally (plaster) or in other forms.

The compounds of formula I and the pharmaceutically acceptable salts of the compounds of formula I can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules. Suitable carriers for the production of solutions and syrups are water, polyols, glycerol, vegetable oil and the like. Suitable carriers for suppositories are, for example, natural or hardened oils, waxes, fats, semi-liquid or liquid polyols and the like.

Moreover, the pharmaceutical preparations can also contain preservatives, solubilizers, stabilizers, wetting agents, emulsifiers, sweeteners, colorants, flavorants, salts for varying the osmotic pressure, puffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for the making of such, which comprises bringing one or more compounds of formula I and/or pharmaceutically acceptable acid addition salts therefore and, if desired, one or more other therapeutically valuable substances into a galenical administration form together with one or more therapeutically inert carriers.

In accordance with the invention, compounds of formula I as well as their pharmaceutically acceptable salts can be used for the treatment or prevention of Alzheimer's disease in mammals, both in humans and non-humans, and for the production of corresponding medicaments. The dosage can vary within wide limits and will, of course, be fitted to the individual requirements in each particular case. In the case of oral administration the individual dosage lies in a range of about 0.5–500 mg. The daily dosage can be up to 1000 mg of a compound of formula I or the corresponding amount of a pharmaceutically acceptable salt thereof, although the limits can also be exceeded when this is found to be indicated.

The novel compounds of formula IA, for example compounds numbered 66 through 105 as above, can be made according to the following Examples:

EXAMPLE 1

8-(4-Benzyloxy-phenyl)-7-oxo-7H-thieno[2,3-a] quinolizine-10-carboxylic acid (2-methoxy-ethyl)-amide a) 2-(4-Benzyloxy-benzylidene)-malononitrile 14.22 g (67 mmol) of 4-benzyloxybenzaldehyde and 5.31 g (80.4 mmol) of malonodinitrile were suspended in 80 ml of isopropanol in the presence of 0.2 ml of piperidine. In so doing the mixture increased in temperature from 19 to 31° C. A solution resulted, from which a solid was finally obtained. This was filtered off after stirring for 30 min. There were obtained 10.3 g (59%) of 2-(4-benzyloxy-benzylidene)-malononitrile with m.p. 146–148° C.

b) 3-(4-Benzyloxy-phenyl)-oxirane-2,2-dicarbonitrile 5.3 ml of 1.2M aqueous sodium hypochloride solution were added dropwise to a suspension of 1.04 g (4 mmol) of 2-(4-benzyloxybenzylidene)-malononitrile in 12 ml of dioxan while stirring at pH 9–10, the mixture was stirred at room temperature for 1 hour and 2N sulphuric acid was added until a pH of 4.8 was reached. Extraction with ethyl acetate, drying with sodium sulphate and distillation of the solvent gave 1.22 g of 3-(4-benzyloxy-phenyl)-oxirane-2,2-dicarbonitrile as a yellow-brown oil, which was used without further purification for the next step.

MS m/e (%): 276 (M$^+$,11), 91 (100).

c) Methyl 8-[p-(benzyloxy)phenyl]-7-oxo-7H-thieno[2,3-a]quinolizine-10-carboxylate 0.55 g (2 mmol) of the above oil was dissolved in 10 ml of acetone, treated with 0.34 g (2 mmol) of thieno[2,3-c] pyridine-7(6H)-thione and held in an ultrasound bath for 3.5 hours. The solvent was distilled off, the residue was treated with 0.39 ml (6.5 mmol) of methyl propiolate in 20 ml of toluene and the suspension was refluxed overnight. Concentration and chromatography over silica gel with toluene/ ethyl acetate 95:5 yielded 0.25 g (38%) of methyl 8-[p-(benzyloxy)phenyl]-7-oxo-7H-thieno[2,3-a]quinolizine-10-carboxylate with m.p. 169–171° C.

d) 8-[p-(Benzyloxy)phenyl]-7-oxo-7H-thieno[2,3-a] quinolizine-10-carboxylic acid 0.23 g (0.5 mmol) of methyl 8-[p-(benzyloxy)phenyl]-7-oxo-7H-thieno[2,3-a]quinolizine-10-carboxylate in 2 ml of ethanol was stirred overnight under reflux with a solution of 0.06 g of potassium hydroxide in 1.25 ml of water. Acidification to pH 1 with 1 N hydrochloric acid and removal of the precipitate by filtration yielded 1.6 g (72%) of 8-[p-(benzyloxy)phenyl]-7-oxo-7H-thieno[2,3-a]quinolizine-10-carboxylic acid with m.p. 197–199° C.

e) 8-(4-Benzyloxy-phenyl)-7-oxo-7H-thieno[2,3-a] quinolizine-10-carboxylic acid (2-methoxy-ethyl)-amide A suspension of 0.15 mg (0.35 mmol) of 8-[p-(benzyloxy) phenyl]-7-oxo-7H-thieno[2,3-a]quinolizine-10-carboxylic acid in 4 ml of toluene was heated at 50° C. for 4 hours with 0.15 ml (2.1 mmol) of thionyl chloride. After removal of all volatile constituents by distillation the residue was suspended in 5 ml of dioxan, treated with 0.06 g (0.76 mmol) of 2-methoxy-ethylamine and stirred at room temperature for 4 hours. After concentration the residue was taken up in dichloromethane, extracted with water and dried with sodium sulphate. Concentration and washing of the residue with ether gave 0.14 g (74%) of 8-(4-benzyloxy-phenyl)-7-oxo-7H-thieno[2,3-a]quinolizine-10-carboxylic acid (2-methoxy-ethyl)-amide as a yellow solid.

MS-ISP: 485 (M+H)$^+$.

The following compounds were manufactured according to Example 1:

EXAMPLE 2

8-(4-Benzyloxy-phenyl)-7-oxo-7H-thieno[2,3-a] quinolizine-10-carboxylic acid bis-(2-methoxy-ethyl)- amide From 8-[p-(benzyloxy)phenyl]-7-oxo-7H-thieno[2,3-a] quinolizine-10-carboxylic acid with SOCl$_2$ and DMF in toluene. Subsequent treatment with triethylamine and bis(2-methoxyethyl)-amine in dioxan.

MS-ISP: 543 (M+H)$^+$.

EXAMPLE 3

8-(4-Benzyloxy-phenyl)-7-oxo-7H-thieno[2,3-a] quinolizine-10-carboxylic acid ethyl-(2-methoxy-ethyl)- amide From 8-[p-(benzyloxy)phenyl]-7-oxo-7H-thieno[2,3-a]quinolizine-10-carboxylic acid with $SOCl_2$ and DMF in toluene. Then treatment with triethylamine and ethyl-(2-methoxy-ethyl)-amine in dioxan.

MS-ISP: 513 (M+H)$^+$.

EXAMPLE 4
8-(4-Benzyloxy-phenyl)-7-oxo-7H-thieno[2,3-a]quinolizine-10-carboxylic acid isopropyl-(2-methoxy-ethyl)-amide From 8-[p-(benzyloxy)phenyl]-7-oxo-7H-thieno[2,3-a]quinolizine-10-carboxylic acid with $SOCl_2$ and DMF in toluene. Then treatment with triethylamine and isopropyl-(2-methoxy-ethyl)-amine in dioxan.

MS-ISP: 526 (M+H)$^+$.

EXAMPLE 5
8-(4-Benzyloxy-phenyl)-7-oxo-7H-thieno[2,3-a]quinolizine-10-carboxylic acid cyclopropylmethyl-(2-methoxy-ethyl)-amide From 8-[p-(benzyloxy)phenyl]-7-oxo-7H-thieno[2,3-a]quinolizine-10-carboxylic acid with $SOCl_2$ and DMF in toluene. Then treatment with triethylamine and cyclopropylmethyl-(2-methoxy-ethyl)-amine in dichloromethane.

MS-ISP: 538 (M+H)$^+$.

EXAMPLE 6
8-(4-Benzyloxy-phenyl)-7-oxo-7H-thieno[2,3-a]quinolizine-10-carboxylic acid benzyl-(2-methoxy-ethyl)-amide From 8-[p-(benzyloxy)phenyl]-7-oxo-7H-thieno[2,3-a]quinolizine-10-carboxylic acid with $SOCl_2$ and DMF in toluene. Then treatment with triethylamine and benzyl-(2-methoxy-ethyl)-amine in dichloromethane. MS-ISP: 575 (M+H)$^+$.

EXAMPLE 7
8-(4-Benzyloxy-phenyl)-7-oxo-7H-thieno[2,3-a]quinolizine-10-carboxylic acid (2-methoxy-ethyl)-phenyl-amide From 8-[p-(benzyloxy)phenyl]-7-oxo-7H-thieno[2,3-a]quinolizine-10-carboxylic acid with $SOCl_2$ and DMF in toluene. Then treatment with triethylamine and (2-methoxy-ethyl)-phenyl-amine in dichloromethane.

MS-ISP: 561 (M+H)$^+$.

EXAMPLE 8
8-(4-Benzyloxy-phenyl)-7-oxo-7H-thieno[2,3-a]quinolizine-10-carboxylic acid (2-hydroxy-ethyl)-phenyl-amide From 8-[p-(benzyloxy)phenyl]-7-oxo-7H-thieno[2,3-a]quinolizine-10-carboxylic acid with $SOCl_2$ and DMF in toluene. Then treatment with triethylamine and phenylethanolamine in toluene.

MS m/e (%): 546 (M$^+$, 56), 455 (100), 410 (45), 291 (21), 263 (34), 234 (15).

EXAMPLE 9
8-(4-Benzyloxy-phenyl)-2-methyl-7-oxo-7H-thieno[2,3-a]quinolizine-10-carboxylic acid (2-methoxy-ethyl)-phenyl-amide 500 mg (0.89 mmol) of 8-(4-benzyloxy-phenyl)-7-oxo-7H-thieno[2,3-a]quinolizine-10-carboxylic acid (2-methoxy-ethyl)-phenyl-amide in 50 ml of tetrahydrofuran were lithiated at −70° C. with 1.1 ml of 1.6N n-butyllithium solution in hexane. After stirring at −70° C. for 1 hour 0.17 ml (2.68 mmol) of methyl iodide was added thereto and the mixture was left to warm to −20° C. during 5 hours. Then, 20 ml of methanol were added thereto, the mixture was left to warm to room temperature, treated with 40 ml of aqueous buffer solution pH 4 and extracted with dichloromethane. Drying with sodium sulphate, evaporation of the solvent and chromatography over silica gel with ethyl acetate/hexane 1:1 gave 0.18 g (35%) of 8-(4-benzyloxy-phenyl)-2-methyl-7-oxo-7H-thieno[2,3-a]quinolizine-10-carboxylic acid (2-methoxy-ethyl)-phenyl-amide as a yellow foam.

MS-ISP: 575 (M+H)$^+$.

In an analogous manner there were obtained:

EXAMPLE 10
(RS)-8-(4-Benzyloxy-phenyl)-2-(1-hydroxy-ethyl)-7-oxo-7H-thieno[2,3-a]quinolizine-10-carboxylic acid (2-methoxy-ethyl)-phenyl-amide By lithiation of 8-(4-benzyloxy-phenyl)-7-oxo-7H-thieno[2,3-a]quinolizine-10-carboxylic acid (2-methoxy-ethyl)-phenyl-amide and reaction with acetaldehyde.

MS-ISP: 605 (M+H)$^+$.

EXAMPLE 11
8-(4-Benzyloxy-phenyl)-7-oxo-7H-thieno[2,3-a]quinolizine-2,10-dicarboxylic acid 2-dimethylamide 10-[(2-methoxy-ethyl)-phenyl-amide]

By lithiation of 8-(4-benzyloxy-phenyl)-7-oxo-7H-thieno[2,3-a]quinolizine-10-carboxylic acid (2-methoxy-ethyl)-phenyl-amide and reaction with dimethylcarbamoyl chloride.

MS-ISP: 632 (M+H)$^+$.

EXAMPLE 12
8-(4-Benzyloxy-phenyl)-2-bromo-7-oxo-7H-thieno[2.3-a]quinolizine-10-carboxylic acid (2-methoxy-ethyl)-phenyl-amide By lithiation of 8-(4-benzyloxy-phenyl)-7-oxo-7H-thieno[2,3-a]quinolizine-10-carboxylic acid (2-methoxy-ethyl)-phenyl-amide and reaction with bromine.

MS-ISP: 641 (M+H)$^+$.

EXAMPLE 13
8-(4-Benzyloxy-phenyl)-2-ethyl-7-oxo-7H-thieno[2,3-a]quinolizine-10-carboxylic acid (2-methoxy-ethyl)-phenyl-amide By lithiation of 8-(4-benzyloxy-phenyl)-7-oxo-7H-thieno[2,3-a]quinolizine-10-carboxylic acid (2-methoxy-ethyl)-phenyl-amide and reaction with ethyl iodide.

MS-ISP: 589 (M+H)$^+$.

EXAMPLE 14
8-(4-Benzyloxy-phenyl)-2-propyl-7-oxo-7H-thieno[2,3-a]quinolizine-10-carboxylic acid (2-methoxy-ethyl)-phenyl-amide By lithiation of 8-(4-benzyloxy-phenyl)-7-oxo-7H-thieno[2,3-a]quinolizine-10-carboxylic acid (2-methoxy-ethyl)-phenyl-amide and reaction with propyl iodide.

MS-ISP: 603 (M+H)$^+$.

EXAMPLE 15
8-(4-Benzyloxy-phenyl)-10-[(2-methoxy-ethyl)-phenyl-carbamoyl]-7-oxo-7H-thieno[2,3-a]quinolizine-2-carboxylic acid By lithiation of 8-(4-benzyloxy-phenyl)-7-oxo-7H-thieno[2,3-a]quinolizine-10-carboxylic acid (2-methoxy-ethyl)-phenyl-amide and reaction with carbon dioxide.

MS-ISP: 605 (M+H)$^+$.

EXAMPLE 16
8-(4-Benzyloxy-phenyl)-2-iodo-7-oxo-7H-thieno[2,3-a]quinolizine-10-carboxylic acid (2-methoxy-ethyl)-phenyl-amide By lithiation of 8-(4-benzyloxy-phenyl)-7-oxo-7H-thieno[2,3-a]quinolizine-10-carboxylic acid (2-methoxy-ethyl)-phenyl-amide and reaction with iodine.

MS-ISP: 687 (M+H)$^+$.

Analogously to Example 1 there were made:

EXAMPLE 17

8-(4-Benzyloxy-phenyl)-7-oxo-7H-thieno[2,3-a]quinolizine-10-carboxylic acid 4-diethylamino-benzyl-amide From 8-[p-(benzyloxy)phenyl]-7-oxo-7H-thieno[2,3-a]quinolizine-10-carboxylic acid with 4-diethylaminomethyl-benzylamine, N-methyl-morpholine, 1-hydroxybenzotriazole and N-(3-dimethylaminopropyl)-N'-ethyl-carbodiimide hydrochloride in dimethylformamide.

MS-ISP m/e: 602.3 (M+H)$^+$.

EXAMPLE 18

8-(4-Benzyloxy-phenyl)-2-bromo-7-oxo-7H-thieno[2,3-a]quinolizine-10-carboxylic acid (2-methoxy-ethyl)-phenyl-amide By lithiation of 8-(4-benzyloxy-phenyl)-7-oxo-7H-thieno[2,3-a]quinolizine-10-carboxylic acid (2-methoxy-ethyl)-phenyl-amide and reaction with bromine.

MS-ISP: 641 (M+H)$^+$.

EXAMPLE 19

8-(4-Benzyloxy-phenyl)-5-bromo-7-oxo-7H-thieno[2,3-a]quinolizine-10-carboxylic acid (2-methoxy-ethyl)-phenyl-amide This compound results in the bromination according to Example 18.

MS-ISP: 641 (M+H)$^+$.

EXAMPLE 20

8-(4-Benzyloxy-phenyl)-2,5-dibromo-7-oxo-7H-thieno[2,3-a]quinolizine-10-carboxylic acid (2-methoxy-ethyl)-phenyl-amide This compound results in the bromination according to Example 18.

MS-ISP: 719 (M+H)$^+$.

EXAMPLE 21

8-(4-Benzyloxy-phenyl)-7-oxo-2-trifluoromethyl-7H-thieno[2,3-a]quinolizine-10-carboxylic acid (2-methoxy-ethyl)-phenyl-amide From 8-(benzyloxy-phenyl)-7-oxo-7H-thieno[2,3-a]quinolizine-10-carboxylic acid (2-methoxy-ethyl)-phenyl-amide by reaction with bis(trifluoroacetyl) peroxide.

MS m/e (%): 628 (39, M$^+$), 537 (100), 478 (16), 382 (36), 331 (26), 263 (10), 1 (13).

EXAMPLE 22

8-(4-Benzyloxy-phenyl)-7-oxo-7H-thieno[2,3-a]quinolizine-10-carboxylic acid (2-methoxy-ethyl)-pyridin-3-ylmethyl-amide From 8-[p-(benzyloxy)phenyl]-7-oxo-7H-thieno[2,3-a]quinolizine-10-carboxylic acid with SOCl$_2$ and DMF in toluene. Then treatment with triethylamine and (2-methoxy-ethyl)-pyridin-3-ylmethyl-amine in dichloromethane.

MS m/e (%): 575 (M$^+$, 41), 484 (100), 263 (16).

The hydrochloride melts at 185–186° C., the methane-sulphonate at 182–185° C.

EXAMPLE 23

8-(4-Benzyloxy-phenyl)-7-oxo-7H-thieno[2,3-a]quinolizine-10-carboxylic acid (2-morpholin-4-yl-ethyl)-phenyl-amide From 8-[p-(benzyloxy)phenyl]-7-oxo-7H-thieno[2,3-a]quinolizine-10-carboxylic acid with SOCl$_2$ and DMF in toluene. Then treatment with triethylamine and (2-morpholin-4-yl-ethyl)-phenyl-amine in dichloromethane. M.p. 168–170° C.

MS m/e (%): 615 (M$^+$, 49), 502 (45), 411 (62), 263 (26), 100 (100).

The methanesulphonate melts at 222–225° C.

EXAMPLE 24

8-(4-Benzyloxy-phenyl)-7-oxo-7H-thieno[2,3-a]quinolizine-10-carboxylic acid 4-diethylamino-benzyl-amide From 8-[p-(benzyloxy)phenyl]-7-oxo-7H-thieno[2,3-a]quinolizine-10-carboxylic acid with 4-diethylamino-benzylamine, N-methylmorpholine, 1-hydroxybenzotriazole and N-(3-dimethylaminopropyl)-N'-ethyl-carbodiimide hydrochloride in dimethylformamide.

M.p.: 191° C.

MS-ISP m/e: 588.4 (M+H)$^+$.

EXAMPLE 25

8-(4-Benzyloxy-phenyl)-7-oxo-7H-thieno[2, 3-a]quinolizine-10-carboxylic acid (2-methoxy-ethyl)-pyrimidin-2-yl-amide From 8-[p-(benzyloxy)phenyl]-7-oxo-7H-thieno[2,3-a]quinolizine-10-carboxylic acid with SOCl$_2$ in toluene. Then treatment with triethylamine and (2-ethoxy-ethyl)-pyrimidin-2-yl-amine in dichloromethane.

MS m/e (%): 562 (M$^+$, 46), 471 (100), 263 (20), 234 (12), 91 (8).

EXAMPLE 26

8-(4-Benzyloxy-phenyl)-7-oxo-7H-thieno[2,3-a]quinolizine-10-carboxylic acid (2-methoxy-ethyl)-(3-methyl-isothiazol-5-yl)-amide a) (2-Methoxy-ethyl)-(3-methyl-isothiazol-5-yl)-amine From methoxyacetyl chloride and 3-methyl-isothiazol-5-ylamine hydrochloride with triethylamine in dichloromethane. Then treatment with a borane-dimethyl sulphide complex in tetrahydrofuran.

1H NMR (250 MHz, CDCl3) d 6.00 (1H, s), 4.84 (1H, br s), 3.60 (2H, t, J=7 Hz), 3.38 (3H, s), 3.23 (2H, q, J=7 Hz), 2.31 (3H, s).

b) 8-(4-Benzyloxy-phenyl)-7-oxo-7H-thieno[2,3-a]quinolizine-10-carboxylic acid (2-methoxy-ethyl)-(3-methyl-isothiazol-5-yl)-amide From 8-[p-(benzyloxy)phenyl]-7-oxo-7H-thieno[2,3-a]quinolizine-10-carboxylic acid and (2-methoxy-ethyl)-(3-methyl-isothiazol-5-yl)-amine with triethylamine and diethyl cyanophosphonate in dimethylformamide.

MS m/e (%): 581 (M$^+$, 40), 490 (36), 410 (100), 291 (20), 263 (35), 234 (20), 91 (15).

EXAMPLE 27

Methyl 8-(biphenyl-4-yl)-7-oxo-7H-thieno[2,3-a]quinolizine-10-carboxylate

Starting from biphenyl-4-carbaldehyde there was obtained methyl 8-(biphenyl-4-yl)-7-oxo-7H-thieno[2,3-a]quinolizine-10-carboxylate.

MS m/e: 411 (M$^+$, 100%).

EXAMPLE 28

8-(Biphenyl-4-yl)-7-oxo-7H-thieno[2,3-a]quinolizine-10-carboxylic acid ethyl-(2-methoxy-ethyl)-amide a) Saponification of methyl 8-(biphenyl-4-yl)-7-oxo-7H-thieno[2,3-a]-quinolizine-10-carboxylate (Example 27) yielded 8-(biphenyl-4-yl)-7-oxo-7H-thieno[2,3-a]quinolizine-10-carboxylic acid.

MS m/e (%): 397 (M⁺, 23), 353 (100), 325 (47).

b) From 8-(biphenyl-4-yl)-7-oxo-7H-thieno[2,3-a] quinolizine-10-carboxylic acid with SOCl₂ in toluene and treatment with triethylamine and ethyl-(2-methoxy-ethyl)-amine in dichloromethane there was obtained 8-(biphenyl-4-yl)-7-oxo-7H-thieno[2,3-a]quinolizine-10-carboxylic acid ethyl-(2-methoxy-ethyl)-amide.

MS m/e (%): 482 (M⁺, 100),439 (6), 424 (12), 380 (54), 352 (23), 324 (537), 145 (23).

EXAMPLE 29

Ethyl 8-(biphenyl-4-yl)-7-oxo-7H-thieno[2,3-a]quinolizine-10-carboxylate

From 8-(biphenyl-4-yl)-7-oxo-7H-thieno[2,3-a] quinolizine-10-carboxylic acid with SOCl₂ in toluene and ethanol.

MS m/e (%): 425 (M⁺, 100), 397 (8), 369 (25), 352 (10), 325 (11).

EXAMPLE 30

8-(Biphenyl-4-yl)-7-oxo-7H-thieno[2,3-a]quinolizine-10-carboxylic acid bis-(2-methoxy-ethyl)-amide From 8-(biphenyl-4-yl)-7-oxo-7H-thieno[2,3-a] quinolizine-10-carboxylic acid with SOCl₂ in toluene. Then treatment with triethylamine and bis(2-methoxyethyl)amine in dichloromethane.

MS m/e (%): 512 (M⁺, 100),469 (12), 454 (20), 380 (73), 352 (15), 324 (35), 145 (20).

Analogously to Example 1 there were made:

EXAMPLE 31 ethyl 7-oxo-8-(4-phenoxy-phenyl)-7H-thieno[2,3-a] quinolizine-10-carboxylate

Starting from 4-phenoxybenzaldehyde there was obtained methyl 7-oxo-8-(4-phenoxy-phenyl)-7H-thieno[2,3-a] quinolizine-10-carboxylate.

MS m/e (%): 427 (M⁺, 100), 399 (22), 368 (13).

EXAMPLE 32

7-Oxo-8-(4-phenoxy-phenyl)-7H-thieno[2,3-a]quinolizine-10-carboxylic acid bis-(2-methoxy-ethyl)-amide a) By saponification of methyl 7-oxo-8-(4-phenoxy-phenyl)-7H-thieno[2,3-a]quinolizine-10-carboxylate there was obtained 7-oxo-8-(4-phenoxy-phenyl)-7H-thieno[2,3-a] quinolizine-10-carboxylic acid.

MS m/e (%): 369 (M⁺, 100), 341 (34), 264 (15).

b) From 7-oxo-8-(4-phenoxy-phenyl)-7H-thieno[2,3-a] quinolizine-10-carboxylic acid with SOCl₂ in toluene and treatment with triethylamine and bis(2-methoxyethyl)amine in dichloromethane there was obtained 7-oxo-8-(4-phenoxy-phenyl)-7H-thieno[2,3-a]quinolizine-10-carboxylic acid bis-(2-methoxy-ethyl)-amide.

MS-ISP: 529 (M+H)⁺.

EXAMPLE 33

7-Oxo-8-(4-phenoxy-phhenyl)-7H-thieno[2,3-a] quinolizine-10-carboxylic acid (2-methoxy-ethyl)-amide From 7-oxo-8-(4-phenoxy-phenyl)-7H-thieno[2,3-a] quinolizine-10-carboxylic acid with SOCl₂ in toluene and treatment with triethylamine and 2-methoxy-ethylamine in dichloromethane there was obtained 7-oxo-8-(4-phenoxy-phenyl)-7H-thieno[2,3-a]quinolizine-10-carboxylic acid (2-methoxy-ethyl)-amide.

MS-ISP: 471 (M+H)⁺.

EXAMPLE 34

7-Oxo-8-(4-phenoxy-phenyl)-7H-thieno[2,3-a]quinolizine-10-carboxylic acid ethyl-(2-methoxy-ethyl)-amide From 7-oxo-8-(4-phenoxy-phenyl)-7H-thieno[2,3-a] quinolizine-10-carboxylic acid with SOCl₂ in toluene and treatment with triethylamine and ethyl-(2-methoxy-ethyl)-amine in dichloromethane there was obtained 7-oxo-8-(4-phenoxy-phenyl)-7H-thieno[2,3-a]quinolizine-10-carboxylic acid ethyl-(2-methoxy-ethyl)-amide.

MS-ISP: 499 (M+H)⁺.

EXAMPLE 35

7-Oxo-8-(4-phenoxy-phenyl)-7H-thieno[2,3-a]quinolizine-10-carboxylic acid benzyl-(2-methoxy-ethyl)-amide From 7-oxo-8-(4-phenoxy-phenyl)-7H-thieno[2,3-a] quinolizine-10-carboxylic acid with SOCl₂ and DMF in toluene and treatment with triethylamine and benzyl-(2-methoxy-ethyl)-amine in dichloromethane there was obtained 7-oxo-8-(4-phenoxy-phenyl)-7H-thieno[2,3-a] quinolizine-10-carboxylic acid benzyl-(2-methoxy-ethyl)-amide.

MS-ISP: 561 (M+H)⁺.

EXAMPLE 36

7-Oxo-8-(4-phenoxy-phenyl)-7H-thieno[2,3-a]quinolizine-10-carboxylic acid (2-methoxy-ethyl)-phenyl-amide From 7-oxo-8-(4-phenoxy-phenyl)-7H-thieno[2,3-a] quinolizine-10-carboxylic acid with SOCl₂ and DMF in toluene and treatment with triethylamine and (2-methoxy-ethyl)-phenyl-amine in dichloromethane there was obtained 7-oxo-8-(4-phenoxy-phenyl)-7H-thieno[2,3-a]quinolizine-10-carboxylic acid (2-methoxy-ethyl)-phenyl-amide.

MS-ISP: 547 (M+H)⁺.

EXAMPLE 37

8-(4-Benzyloxy-phenyl)-3-methyl-7-oxo-3,7-dihydro-imidazo[4,5-a]quinolizine-10-carboxylic acid (2-methoxy-ethyl)-phenyl-amide a) 8-(4-Benzyloxy-phenyl)-3-methyl-7-oxo-3,7-dihydro-imidazo[4,5-a]quinolizine-10-carboxylic acid 2.44 g (5.5 mmol) of methyl 8-(4-benzyloxy-phenyl)-3-methyl-7-oxo-3,7-dihydro-imidazo[4,5-a]quinolizine-10-carboxylate in 50 ml of ethanol were treated with a solution of 1.4 g (21 mmol) of potassium hydroxide (content 86%) in 50 ml of water. After boiling under reflux for 4 hours 200 ml of water were added and the mixture was adjusted to pH 1–2 with 2N hydrochloric acid while cooling with ice. The precipitate obtained was filtered off, washed with water and dried. There were obtained 2.16 g (92%) of 8-(4-benzyloxy-phenyl)-3-methyl-7-oxo-3,7-dihydro-imidazo[4,5-a] quinolizine-10-carboxylic acid as yellow crystals with m.p. 227–229° C.

b) Methyl 8-(4-benzyloxy-phenyl)-3-methyl-7-oxo-3,7-dihydro-imidazo[4,5-a]quinolizine-10-carboxylate 3.50 g (21.2 mmol) of 1-methyl-1,5-dihydro-imidazo[4,5-c]pyridine-4-thione were dissolved in 0.6 1 of 1,3-dimethyl-2-imidazolidinone at 140° C., left to cool to room temperature, treated with 5.9 g (21.4 mmol) of 3-(3-benzyloxyphenyl)-oxirane-2,2-dicarbonitrile and stirred over the weekend. Then, 7.8 ml of methyl propiolate were added and the mixture was stirred at 110° C. for 22 hours. After cooling the solution was stirred into 6 1 of water, the precipitate was filtered off and it was chromatographed over silica gel with dichloromethane/acetone/hexane 2:1:1. There were obtained 3.20 g (34%) of methyl 8-(4-benzyloxy-phenyl)-3-methyl-7-oxo-3,7-dihydro-imidazo[4,5-a] quinolizine-10-carboxylate as yellow crystals with m.p 196–198° C.

c) 1-Methyl-1,5-dihydro-imidazo[4,5-c]pyridine-4-thione 4.00 g (23.9 mmol) of 4-chloro-1-methyl-1H-imidazo[4, 5-c]pyridine in 27 ml of dimethylformamide were stirred at 115° C. for 18 hours with 8.10 g (95.6 mmol) of sodium hydrogen sulphide hydrate. After cooling the mixture was treated with 110 ml of water, adjusted to pH 4 with acetic acid and stirred at 5° C. while cooling with ice for 15 min. The precipitate was filtered off and washed with water. After drying there were obtained 3.73 g (95%) of 1-methyl-1,5-dihydro-imidazo[4,5-c]pyridine-4-thione as white crystals with m.p.>300° C.

MS m/e (%): 165 (M$^+$, 100), 150 (3), 136 (12), 132 (5), 123 (5).

d) From 8-(4-benzyloxy-phenyl)-3-methyl-7-oxo-3,7-dihydro-imidazo [4,5-a]quinolizine-10-carboxylic acid with SOCl$_2$ and DMF in toluene and treatment with triethylamine and (2-methoxy-ethyl)-phenyl-amine in dichloromethane.

MS-ISP: 559 (M+H)$^+$.

EXAMPLE 38

8-(4-Benzyloxy-phenyl)-3-methyl-7-oxo-3,7-dihydro-imidazo [4,5-a]quinolizine-10-carboxylic acid bis-(2-methoxy-ethyl)-amide From 8-(4-benzyloxy-phenyl)-3-methyl-7-oxo-3,7-dihydro-imidazo[4,5-a]quinolizine-10-carboxylic acid with SOCl$_2$ in toluene and treatment with triethylamine and bis(2-methoxyethyl)amine in dichloromethane.

MS-ISP: 541 (M+H)$^+$.

EXAMPLE 39

8-(4-Benzyloxy-phenyl)-3-methyl-7-oxo-3,7-dihydro-imidazo[4,5-a]quinolizine-10-carboxylic acid cyclopropylmethyl-(2-methoxy-ethyl)-amide From 8-(4-benzyloxy-phenyl)-3-methyl-7-oxo-3,7-dihydro-imidazo[4,5-a]quinolizine-10-carboxylic acid with SOCl$_2$ and DMF in toluene and treatment with triethylamine and cyclopropylmethyl-(2-methoxy-ethyl)-amine in dichloromethane.

MS-ISP: 537 (M+H)$^+$.

EXAMPLE 40

8-(4-Benzyloxy-phenyl)-3-methyl-7-oxo-3,7-dihydro-imidazo[4 5-a]quinolizine-10-carboxylic acid (2-methoxy-ethyl)-propyl-amide From 8-(4-benzyloxy-phenyl)-3-methyl-7-oxo-3,7-dihydro-imidazo[4,5-a]quinolizine-10-carboxylic acid with SOCl$_2$ and DMF in toluene and treatment with triethylamine and (2-methoxy-ethyl)-propyl-amine in dichloromethane.

MS-ISP: 525 (M+H)$^+$.

EXAMPLE A

Tablets of the following composition are produced in a conventional manner:

|  | mg/tablet |
|---|---|
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in the usual manner:

|  | mg/tablet |
|---|---|
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/capsule |
|---|---|
| Active ingredient | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The finished mixture is filled into hard gelatine capsules of suitable size.

We claim:

1. A compound of the formula

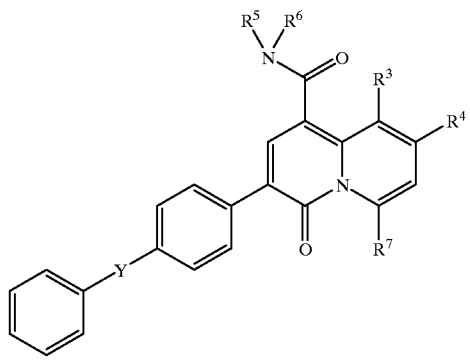

IA wherein
R$^3$ and R$^4$ each represent hydrogen or together represent one of the groups —S—CH═CH—, —CH═CH—S—, —CH═CH—CH═CH—, —CH═CCl—CH═CH—, —N═CHN(CH$_3$)—, —S—C[CH(OH)(CH$_3$)]═CH—, —S—C(carbamoyl)═CH—, —S—C(halogen)═CH—, —S—C[C(O)OH]═CH—, —S—C(lower-alkyl)═CH— or —NH(o-phenylene);
R$^5$ represents hydrogen, lower-alkyl, lower-alkenyl, lower-alkynyl, lower-alkoxy, lower-alkoxy-alkyl, phenyl optionally substituted by lower-alkoxy, hydroxyalkyl, cycloalkyl optionally substituted by hydroxy or lower-alkoxy, benzyl optionally substituted by di-lower-alkylaminoalkyl, lower-alkanoyldialkylamino, lower-alkynyldialkylamino, lower-alkenyldialkylamino, lower-alkyldialkylamino or a saturated or aromatic 4 to 6-membered ring with at least one N, O and/or S atom, or a saturated or aromatic bicyclic residue with optionally 1–3 hetero atoms, with the rings being bonded directly or via an alkylene, alkenylene or alkynylene group and being optionally substituted by one or more substituents from lower-alkyl, lower-alkoxy, hydroxy, oxo, benzyloxycarbonyl or lower-alkanoyloxyalkyl;

$R^6$ signifies hydrogen, lower-alkyl, lower-alkoxy-alkyl, cycloalkyl-lower-alkyl, phenyl, benzyl or lower-alkoxy, and wherein when $Q^1$ is $NR^6$, $R^5$ and $R^6$ together can form a 4–6-membered saturated or aromatic heterocyclic ring with 1–2 N atoms, which is optionally substituted by one or more substituents selected from lower-alkoxy, lower-alkoxyalkyl, lower-hydroxyalkyl, hydroxy, halogen, lower-haloalkyl, lower-alkanoyloxyalkyl, lower-alkyl, haloalkyl or oxo; and $R^7$ signifies hydrogen or halogen;

and Y signifies a bond, —O—, —O-lower-alkyl or lower-alkyl-O—, as well as their pharmaceutically acceptable salts.

2. A compound of claim 1, wherein the compound is selected from 8-(4-Benzyloxy-phenyl)-7-oxo-7H-thieno[2,3-a]quinolizine-10-carboxylic acid (2-methoxy-ethyl)-phenyl-amide, 8-(4-Benzyloxy-phenyl)-2-methyl-7-oxo-7H-thieno[2,3-a]quinolizine-10-carboxylic acid (2-methoxy-ethyl)-phenyl-amide or 8-(4-Benzyloxy-phenyl)-7-oxo-7H-thieno[2,3-a]quinolizine-10-carboxylic acid (2-methoxy-ethyl)-pyrimidine-2-yl-amide.

3. A pharmaceutical composition comprising a compound of formula IA

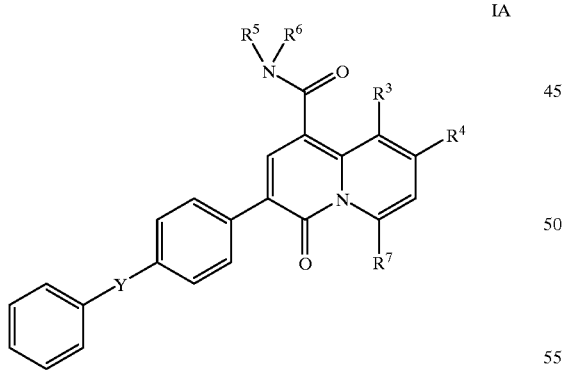

IA wherein $R^3$ and $R^4$ each represent hydrogen or together represent one of the groups —S—CH=CH—, —CH=CH—S—, —CH=CH—CH=CH—, —CH=CCl—CH=CH—, —N=CHN(CH$_3$)—, —S—C[CH(OH)(CH$_3$)]=CH—, —S—C(carbamoyl)=CH—, —S—C(halogen)=CH—, —S—C[C(O)OH]=CH—, —S—C(lower-alkyl)=CH— or —NH(o-phenylene);

$R^5$ represents hydrogen, lower-alkyl, lower-alkenyl, lower-alkynyl, lower-alkoxy, lower-alkoxy-alkyl, phenyl optionally substituted by lower-alkoxy, hydroxyalkyl, cycloalkyl optionally substituted by hydroxy or lower-alkoxy, benzyl optionally substituted by di-lower-alkylaminoalkyl, lower-alkanoyldialkylamino, lower-alkynyldialkylamino, lower-alkenyldialkylamino, lower-alkyldialkylamino or a saturated or aromatic 4 to 6-membered ring with at least one N, O and/or S atom, or a saturated or aromatic bicyclic residue with optionally 1–3 hetero atoms, with the rings being bonded directly or via an alkylene, alkenylene or alkynylene group and being optionally substituted by one or more substituents from lower-alkyl, lower-alkoxy, hydroxy, oxo, benzyloxycarbonyl or lower-alkanoyloxyalkyl;

$R^6$ signifies hydrogen, lower-alkyl, lower-alkoxy-alkyl, cycloalkyl-lower-alkyl, phenyl, benzyl or lower-alkoxy, and wherein when $Q^1$ is —$NR^6$—, $R^5$ and $R^6$ together can form a 4–6-membered saturated or aromatic heterocyclic ring with 1–2 N atoms, which is optionally substituted by one or more substituents selected from lower-alkoxy, lower-alkoxyalkyl, lower-hydroxyalkyl, hydroxy, halogen, lower-haloalkyl, lower-alkanoyloxyalkyl, lower-alkyl, haloalkyl or oxo; and $R^7$ signifies hydrogen or halogen;

and Y signifies a bond, —O—, —O-lower-alkyl or lower-alkyl-O—, as well as their pharmaceutically acceptable salts, and a pharmacaceutically acceptable carrier.

4. A method of inhibiting β-amyloid peptide activity in connection with treating or preventing Alzheimer's disease in a mammal in need of such treatment comprising to said mammal a therapeutically effective amount of a compound of formula IA

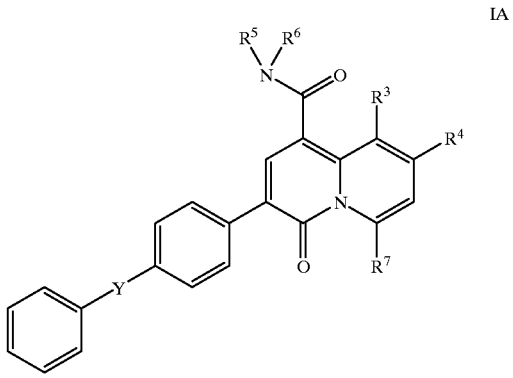

IA

Wherein $R^3$ and $R^4$ each represent hydrogen or together represent one of the groups —S—CH=CH—, —CH=CH—S—, —CH=CH—CH=CH—, —CH=CCl—CH=CH—, —N=CHN(CH$_3$)—, —S—C[(CH(OH)(CH$_3$)]=CH—, —S—C(carbamoyl)=CH—, —S—C(halogen)=CH—, —S—C[C(O)OH]=CH—, —S—C(lower-alkyl)=CH— or —NH(o-phenylene);

$R^5$ represents hydrogen, lower-alkyl, lower-alkenyl, lower-alkynyl, lower-alkoxy, lower-alkoxy-alkyl, phenyl optionally substituted by lower-alkoxy, hydroxyalkyl, cycloalkyl optionally substituted by hydroxy or lower-alkoxy, benzyl optionally substituted by di-lower-alkylaminoalkyl, lower-alkanoyldialkylamino, lower-alkynyldialkylamino, lower-alkenyldialkylamino, lower-alkyldialkylamino or a saturated or aromatic 4 to 6-membered ring with at least one N, O and/or S atom, or a saturated or aromatic bicyclic residue with optionally 1–3 hetero atoms, with the rings being bonded directly or via an alkylene, alkenylene or alkynylene group and being optionally substituted by one or more substituents from lower-alkyl, lower-alkoxy, hydroxy, oxo, benzyloxycarbonyl or lower-alkanoyloxyalkyl;

$R^6$ signifies hydrogen, lower-alkyl, lower-alkoxy-alkyl, cycloalkyl-lower-alkyl, phenyl, benzyl or lower-alkoxy, and wherein when $Q^1$ is —$NR^6$—, $R^5$ and $R^6$ together can form a 4–6-membered saturated or aromatic heterocyclic ring with 1–2 N atoms, which is optionally substituted by one or more substituents selected from lower-alkoxy, lower-alkoxyalkyl, lower-hydroxyalkyl, hydroxy, halogen, lower-haloalkyl, lower-alkanoyloxyalkyl, lower-alkyl, haloalkyl or oxo; and $R^7$ signifies hydrogen or halogen;

and Y signifies a bond, —O—, —O-lower-alkyl or lower-alkyl-O—, as well as their pharmaceutically acceptable salts, and a pharmaceutically acceptable carrier.

* * * * *